United States Patent
Sulley et al.

(10) Patent No.: US 9,642,794 B2
(45) Date of Patent: May 9, 2017

(54) ANTIVIRAL PHARMACEUTICAL FOR TOPICAL ADMINISTRATION

(71) Applicant: Tamir Biotechnology, Inc., San Diego, CA (US)

(72) Inventors: Jamie Sulley, Old Saybrook, CT (US); Luis Squiquera, Buenos Aires, AR (US)

(73) Assignee: Tamir Biotechnology, Inc., Short Hills, NJ (US)

( * ) Notice: Subject to any disclaimer, the term of this patent is extended or adjusted under 35 U.S.C. 154(b) by 34 days.

(21) Appl. No.: 14/793,920

(22) Filed: Jul. 8, 2015

(65) Prior Publication Data
US 2016/0045431 A1    Feb. 18, 2016

Related U.S. Application Data

(63) Continuation-in-part of application No. 14/462,520, filed on Aug. 18, 2014.

(51) Int. Cl.
A61K 38/46   (2006.01)
A61K 9/00    (2006.01)
A61F 6/00    (2006.01)
A61F 6/08    (2006.01)

(52) U.S. Cl.
CPC .......... *A61K 9/0014* (2013.01); *A61K 9/0034* (2013.01); *A61K 38/465* (2013.01); *C12Y 301/27005* (2013.01); *C12Y 301/27* (2013.01)

(58) Field of Classification Search
None
See application file for complete search history.

(56) References Cited

U.S. PATENT DOCUMENTS

| | | | |
|---|---|---|---|
| 8,663,964 B2* | 3/2014 | Saxena | A61K 38/46 424/94.1 |
| 2009/0202513 A1 | 8/2009 | Ramos-Nino | |
| 2011/0274704 A1 | 11/2011 | Chang | |
| 2012/0260922 A1* | 10/2012 | Gomez-Acebo | A61K 9/0014 128/844 |
| 2013/0022589 A1 | 1/2013 | Saxena | |
| 2014/0128396 A1* | 5/2014 | Schadt | C07D 401/10 514/236.5 |

OTHER PUBLICATIONS

Porta et al., 2008. Ranpirnase and its potential for the treatment of unresectable malignant mesothelioma. Biologics: Targets & Therapy, vol. 2(4):601-609.*
Wu et al., 1993. A Cytotoxic Ribonuclease: Study of the Mechanism of Onconase Cytotoxicity. The Journal of Biological Chemistry, vol. 268, No. 14, pp. 10686-10693). Wu et al., teach that Onconase, or P-30, an RNAse (p. 10686, col. 1, Lines 10-15.*

* cited by examiner

*Primary Examiner* — Debbie K Ware
*Assistant Examiner* — Kailash C Srivastava
(74) *Attorney, Agent, or Firm* — Mark H. Jay; Mark H. Jay, P.A.

(57) ABSTRACT

An enzymatically-active ribonuclease is combined with a vehicle that does not unacceptably interfere with such enzymatic activity and applied externally. Advantageously, the ribonuclease is ranpirnase. The vehicle can be a liquid, a gel, an ointment, or a serum, and can also be an approved sexual lubricant.

7 Claims, 2 Drawing Sheets

FIG. 1

| TREATMENT ARM | | CLINICAL HEALING | 25% IMPROVEMENT | 50% IMPROVEMENT |
|---|---|---|---|---|
| FORMULATION A, n= 13 ENROLLED | VISIT 1-4 (n=13) | 4 (30.8%) | 3 (23.1%) | 6 (46.2%) |
| | VISIT 5-8 (n=8) | 8 (100%) | 0 | 0 |
| FORMULATION B, n= 8 ENROLLED | VISIT 1-4 (n=7) | 0 | 1 (14.3%) | 6 (85.7%) |
| | VISIT 5-8 (n=6) | 5 (83.3%) | 0 | 1 (16.7%) |
| FORMULATION C, n= 13 ENROLLED | VISIT 1-4 (n=11) | 3 (27.3%) | 1 (9.1%) | 7 (63.6%) |
| | VISIT 5-8 (n=7) | 7 (100%) | 0 | 0 |
| TOTAL EVALUABLE PATIENTS FROM ALL THREE ARMS | VISIT 1-4 (n=31) | 7 (22.6%) | 5 (16.1%) | 19 (61.3%) |
| | VISIT 5-8 (n=21) | 20 (95.2%) | 0 | 1 (4.7%) |

* PERCENTAGES BASED ON NUMBER OF EVALUABLE PATIENTS AT EACH TIMEPOINT

ANTIVIRAL PHARMACEUTICAL FOR TOPICAL ADMINISTRATION

BACKGROUND OF THE INVENTION

The invention relates to antiviral pharmaceuticals, and more particularly relates to antiviral pharmaceuticals for topical administration. In its most immediate sense, the invention relates to pharmaceuticals for treating patients with anogenital warts.

Ranpirnase is a protein with ribonuclease activity, it has a molecular weight of approximately 12,000 Daltons, and it has an amino acid sequence disclosed and claimed in U.S. Pat. No. 5,559,212. It can be isolated from embryos and eggs of the *Rana pipiens* frog or produced as a recombinant protein (see e.g. U.S. Pat. No. 6,175,003 B1). Commonly-owned U.S. Pat. No. 8,663,964 B2 teaches that ranpirnase and another enzymatically-active ribonuclease are active against human papillomavirus (hereinafter, "HPV") and that HPV can be treated by using either of these two ribonucleases on an HPV-infected region of a patient. Anogenital warts are caused by various human papillomaviruses, and no satisfactory treatment exists for this sexually-transmitted disease since all available treatment modalities target the lesions and lack viricidal activity against HPV.

It has been proposed to treat anogenital warts intralesionally, i.e. by injecting an active pharmaceutical ingredient ("API") into the wart to be treated. In many situations—where the warts are small or too numerous, or in locations where an injection would be too painful—this would be unsatisfactory.

It has also been proposed to treat anogenital warts topically. Because the HPV-infected cells are located beneath the surface of the patient's skin and would not be directly contacted by the API, this proposal assumed that it would be necessary to administer the API using a special vehicle that would penetrate through the intervening layers of the patient's skin to thereby deliver the API to a location where its anti-HPV activity would be useful.

A Phase I compassionate use observational study was carried out in Argentina on male volunteers with anogenital warts. Commonly-owned parent patent application Ser. No. 14/462,520 filed Aug. 18, 2014 discloses an unexpected and surprising result from this study, namely, that it is unnecessary to administer the API using a vehicle that would penetrate through the layers of the patient's skin. Rather, that study demonstrated that topical ranpirnase therapy for HPV did not—as was expected—require a vehicle having penetrating characteristics. Rather, it appeared that the vehicle need only not unacceptably interfere with the enzymatic activity of ranpirnase. Furthermore, because there are other enzymatically-active ribonucleases that behave similarly to ranpirnase, the referenced parent patent application stated that it was reasonable to expect that any such ribonuclease would, when combined with a suitable vehicle, have an activity similar to that of ranpirnase.

This Phase I study has now been completed, with most favorable results. While the study lasted for only eight weeks, in more than 80% of the evaluable patients no warts were visible, i.e. those patients appeared to be "clinically healed". To a person of ordinary skill in the art, this is strong evidence that the invention is reasonably correlated with usefulness in treating HPV.

Significantly, it is believed that the vehicle need not be entirely free of anti-enzymatic activity. In some instances, it is believed possible to overcome anti-enzymatic qualities of the carrier by increasing the concentration of the enzymatically-active ribonuclease.

In accordance with the invention, a pharmaceutical comprises a therapeutically effective quantity of an enzymatically-active ribonuclease and a vehicle that does not unacceptably interfere with such enzymatic activity.

Preferred embodiments of the invention use ranpirnase as the enzymatically-active ribonuclease. While an oil in water-based vehicle containing other components such as collagen can be used, preferred embodiments use an aqueous vehicle. Preferred aqueous vehicles are gels, serums, lotions, or approved sexual lubricants (which may themselves be gels or lotions). This is because gels, lotions, serums, and sexual lubricants are viscous or can be made viscous so that the invention will remain where it has been applied and will not run off. Advantageously, and in accordance with preferred embodiments of the invention, the pharmaceutical has between 1 and 3 mg of ranpirnase per ml of vehicle.

BRIEF DESCRIPTION OF THE DRAWING

FIG. 1 shows the global performance of evaluable patients treated with the invention in a Phase I study;

DETAILED DESCRIPTION OF PREFERRED EMBODIMENTS

A Phase I compassionate use clinical study was conducted in Buenos Aires. Male volunteers who were diagnosed with anogenital warts in various locations (scrotum, penis shaft, penis dorsum, inguinal, perianal) were accrued to the study. The study had three arms. In arm A, the tested embodiment was ranpirnase combined with a vehicle supplied by JRX Biotechnology, Inc. (In this instance, the ranpirnase was reconstituted from lyophilized powder.) In arm C, the tested embodiment was also ranpirnase combined with the same JRX Biotechnology, Inc. vehicle, but in this instance the ranpirnase had been previously frozen and was thawed prior to use. These two combinations were very low-viscosity liquids; each was applied topically twice each day. The vehicle used in these two arms is a polysaccharide megasphere formulation; on information and belief it is covered by U.S. Pat. Nos. 6,759,056, 6,946,144, 7,201,919, 7,220,427, 7,300,666, and 7,316,820. In arm B, the tested embodiment was ranpirnase combined with K-Y® Brand Jelly. This second embodiment was formulated from ranpirnase reconstituted from lyophilized powder; it is a viscous gel that was applied topically three times each day. In each arm, the concentration of ranpirnase was 1 mg ranpirnase to 1 ml of vehicle.

As can be seen in FIG. 1, 22.6% of all the patients in the study achieved clinical healing by the 4th week of treatment, with 61.3% of all the patients having reached a 50% improvement by that time. FIG. 1 also shows that 95.2% of all the patients achieved clinical healing by the $8^{th}$ week, with 4.7% of all the patients having reached a 50% improvement in this time. Although the long-term effect of this treatment is not yet known, this short-term effect is far better than has been reported for other pharmaceuticals (Podofilox solution and gel, Aldara Cream, Veregen ointment).

Figure 2:
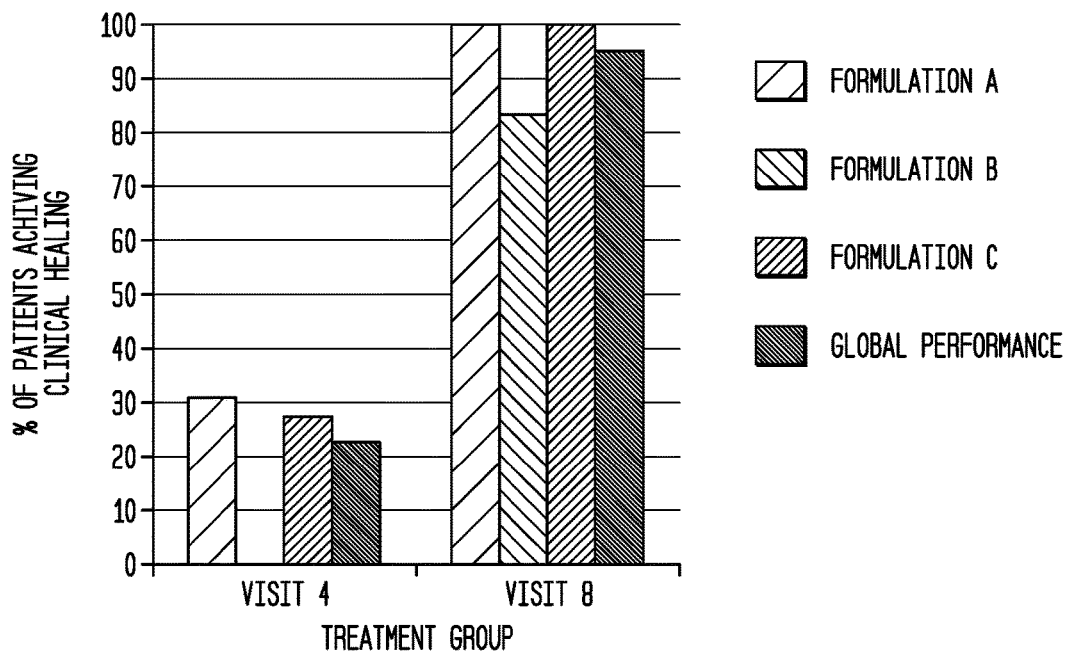
FIG. 2 shows the number of patients who achieved clinical healing at weeks 4 and 8 in the Phase I study.

FIG. 2 graphically displays the information in the three leftmost columns in FIG. 1. To a person of ordinary skill in this art, FIG. 2 is strong evidence that the invention is reasonably correlated with usefulness in treating HPV. FIG. 2 shows that 100% of the evaluable patients in arms A and C achieved clinical healing by the $8^{th}$ week, and 83.3% of the patients in arm B achieved clinical healing by that time. Overall, 95.2% of all patients achieved clinical healing by the $8^{th}$ week.

Figure 3:
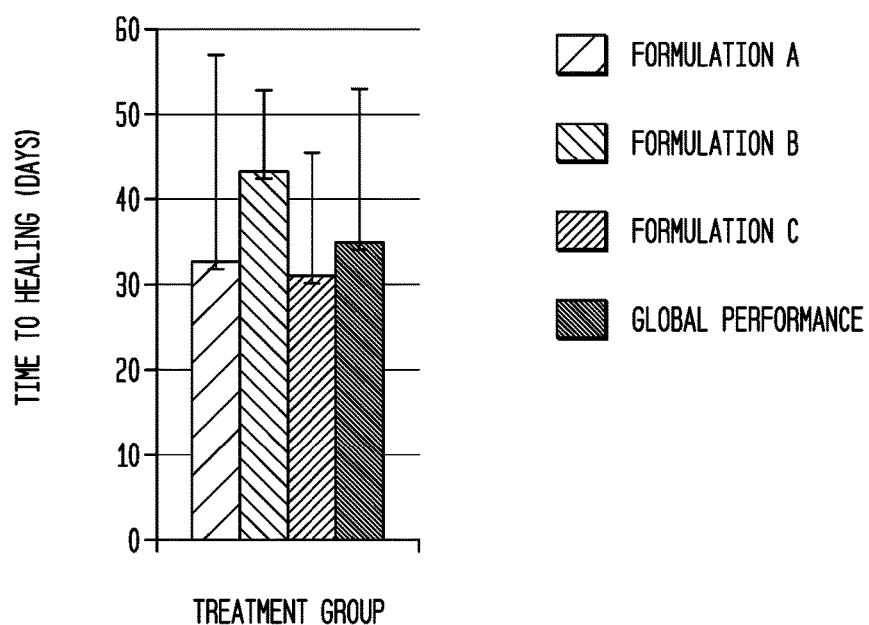
FIG. 3 shows the time required for patients in the Phase I study to reach clinical healing.

FIG. 3 displays the average time required for patients in each of the three arms, and in the study as a whole, to reach clinical healing. The patients in arm B required more than 40 days to reach clinical healing, while the patients in arms A and C reached clinical healing sooner (in approximately 32 and 34 days, respectively).

Although these results may seem to indicate that the second preferred embodiment used in arm B of the study is not as active against HPV as the first preferred embodiment used in arms A and C, the study did not include enough patients to permit such a conclusion to be drawn.

This study did not address the question of dosage; in all arms of the study the quantity of ranpirnase delivered to the patient was 1 mg/week. The activity of the preferred embodiment may be improved by increasing the concentration of ranpirnase from 1 mg/ml to 3 mg/ml, whereby the weekly dose of ranpirnase administered to each patient would be increased to 3 mg, but this has not yet been tested.

It will be understood that although the invention has been developed for use in treatment of anogenital warts, its use is not restricted to this application. The invention may have other antiviral applications. Although the invention is presently applied to external anogenital warts, it may also be useful when applied vaginally, extra-vaginally, intra-vaginally, anally, peri-anally, and intra-anally. Although the preferred embodiment uses ranpirnase as the enzymatically-active ribonuclease, other ribonucleases having similar enzymatic activities exist and may be used instead. Furthermore, while treatment of anogenital warts may be easier using a viscous vehicle such as a gel because it is easier to apply a gel to an anogenital wart and a gel is less likely to run off and is therefore more likely to remain where it has been applied, there may be other applications in which a liquid vehicle, or an ointment vehicle will be preferable. The vehicle may alternatively be a serum, a lotion, or an approved sexual lubricant, i.e. a lubricant that meets applicable governmental requirements and is intended for use on human genitalia.

Although at least one preferred embodiment of the invention has been described above, this description is not limiting and is only exemplary. The scope of the invention is defined only by the claims, which follow:

The invention claimed is:

1. A topical pharmaceutical composition consisting essentially of a therapeutically effective amount of an enzymatically-active ribonuclease and a viscous vehicle that does not unacceptably interfere with the enzymatic activity, wherein the vehicle is selected from the group consisting of a gel, a serum, or a lotion.

2. The pharmaceutical composition of claim 1, wherein the enzymatically-active ribonuclease is ranpirnase.

3. The pharmaceutical composition of claim 2, wherein the pharmaceutical contains between 1 and 3 mg of ranpirnase per ml of vehicle.

4. The pharmaceutical composition of claim 2, wherein the concentration of ranpirnase in the pharmaceutical composition is chosen to deliver between 1 and 3 mg of ranpirnase to the patient each week that the pharmaceutical composition is administered to the patient in accordance with the dosage regimen used.

5. The pharmaceutical composition of claim 1, wherein the vehicle is compatible with latex condoms.

6. The pharmaceutical composition of claim 1, wherein the vehicle is an aqueous vehicle.

7. The pharmaceutical composition of claim 6, wherein the vehicle is an approved sexual lubricant.

* * * * *